United States Patent [19]
Wise et al.

[11] Patent Number: 4,881,410
[45] Date of Patent: Nov. 21, 1989

[54] ULTRAMINIATURE PRESSURE SENSOR AND METHOD OF MAKING SAME

[75] Inventors: Kensall D. Wise; Hin-Leung Chau, both of Ann Arbor, Mich.

[73] Assignee: The Regents of the University of Michigan, Ann Arbor, Mich.

[21] Appl. No.: 190,310

[22] Filed: May 4, 1988

Related U.S. Application Data

[62] Division of Ser. No. 57,884, Jun. 1, 1987, Pat. No. 4,815,472.

[51] Int. Cl.$^4$ ............................ G01L 7/08; G01L 9/12
[52] U.S. Cl. ........................................ 73/724; 73/718; 361/283
[58] Field of Search .................. 73/724, DIG. 4, 718, 73/756; 361/283; 29/59.3, 24.41

[56] References Cited

U.S. PATENT DOCUMENTS

| | | | |
|---|---|---|---|
| 3,397,278 | 8/1968 | Pomerantz | 174/52 |
| 3,951,707 | 4/1976 | Kurtz et al. | 156/3 |
| 4,121,334 | 10/1978 | Wallis | 29/589 |
| 4,261,086 | 4/1981 | Giachino et al. | 29/25.41 |
| 4,420,790 | 12/1983 | Golke et al. | 361/283 |
| 4,426,768 | 1/1984 | Black et al. | 29/583 |
| 4,513,348 | 4/1985 | Grantham | 361/283 |
| 4,517,622 | 5/1985 | Male | 361/283 |
| 4,773,972 | 9/1988 | Mikkor | 73/724 |
| 4,815,472 | 3/1989 | Wise et al. | 73/724 |
| 4,831,492 | 5/1989 | Kuisma | 73/724 |
| 4,838,088 | 6/1989 | Murakami | 73/724 |

OTHER PUBLICATIONS

W. H. Ko, "Development of a Miniature Pressure Transducer for Biomedical Applications," IEEE Transactions on Electron Devices, vol. ED-26, No. 12, pp. 1896–1905, (Dec. 1979).
J. M. Borky and K. D. Wise, "Integrated Signal Conditioning for Silicon Pressure Sensors," IEEE Transactions on Electron Devices, vol. ED-26, No. 12, pp. 1906–1910, (Dec. 1979).
C. S. Sander et al., "A Monolithic Capacitive Pressure Sensor with Pulse-Period Output," IEEE Transactions on Electron Devices, vol. ED-27, No. 5, pp. 927–930, (May 1980).
Y. S. Lee and K. D. Wise, "A Batch-Fabricated Silicon Capacitive Pressure Transducer with Low Temperature Sensitivity," IEEE Transactions on Electron Devices, vol. ED-29, No. 1, pp. 42–48, (Jan. 1982).
W. H. Ko et al., "A High-Sensitivity Integrated-Circuit Capacitive Pressure Transducer," IEEE Transactions on Electron Devices, vol. ED-29, No. 1, pp. 48–56, (Jan. 1982).
M. Esashi et al., "Fabrication of Catheter-Tip and Sidewall Miniature Pressure Sensors," IEEE Transactions on Electron Devices, vol. ED-29, No. 1, pp. 57–63, (Jan. 1982).
B. E. Burns et al., "Fabrication Technology of a Chronic In-Vivo Pressure Sensor," IEDM, San Francisco, Calif., Dec. 1984, pp. 210–212.

(List continued on next page.)

*Primary Examiner*—Donald O. Woodiel
*Attorney, Agent, or Firm*—Harness, Dickey & Pierce

[57] ABSTRACT

A capacitive pressure sensor suitable for making highly sensitive, low pressure measurements is disclosed. The sensor may be mounted into a 0.5 mm OD catheter suitable for multipoint pressure measurements from within the coronary artery of the heart. The sensor employs a transducer which consists of a rectangular bulk silicon micro-diaphragm several hundred microns on a side by two microns thick, surrounded by a supporting bulk silicon rim about 12 microns thick. Both the diaphragm and the rim are defined by a double diffusion etch-stop technique. The transducer fabrication process features a batch wafer-to-glass electrostatic seal followed by a silicon etch, which eliminates handling of individual small diaphragm structures until die separation and final packaging. An addressable read-out interface circuit may be used with the sensor to provide a high-level output signal, and allows the sensor to be compatible for use on a multisite catheter having only two electrical leads.

24 Claims, 7 Drawing Sheets

OTHER PUBLICATIONS

H. Guckel et al., "Laser-Recrystallized Piezoresistive Micro-Diaphragm Sensor," Transducer '85, Philadelphia, Pa., Jun. 1985, pp. 182–185.

R. S. Hijab and R. S. Muller, "Micromechanical Thin-Film Cavity Structures for Low Pressure and Acoustic Transducer Applications," Transducer '85, Philadelphia, Pa., Jun. 1985, pp. 178–181.

K. Najafi, K. D. Wise and T. Mochizuki, "A High-Yield IC-Compatible Multichannel Recording Array," IEEE Transactions on Electron Devices, vol. ED-32, No. 7, pp. 1206–1211, (Jul. 1985).

I. H. Choi and K. D. Wise, "A Silicon-Thermopile-Based Infrared Sensing Array for Use in Automated Manufacturing," IEEE Transactions on Electron Devices, Vol. ED-33, No. 1, pp. 72–79, (Jan. 1986).

K. D. Wise and H. Chau, "Scaling Limits in Batch-Fabricated Silicon Pressure Sensors," IEEE Transactions on Electron Devices, vol. ED-34, No. 4, pp. 850–858, (Apr. 1987).

ULTRAMINIATURE PRESSURE SENSOR AND METHOD OF MAKING SAME

This application is a division of U.S. patent application Ser. No. 057,884 filed June 1, 1987 now U.S. Pat. No 4,815,472.

FIELD OF THE INVENTION

This invention relates in general to solid-state pressure sensors and methods of making them, and in particular to silicon pressure sensors having a diaphragm and supporting rim structure made from monocrystalline silicon wafers processed using etch-stop techniques.

BACKGROUND OF THE INVENTION

There are many applications requiring the accurate measurement of pressure, ranging from the monitoring of physiological parameters for medical research, to the precise control of fluids or gases, to measurement of low energy acoustical signals. Typical applications include industrial process monitoring, such as the monitoring of gas flow under partial vacuums in semiconductor processing facilities to the precise control of air/fuel ratios in automobiles. Typical medical applications include measurement of blood pressure in surgery and in intensive care, air pressure in respiratory diseases, intrauterine pressure in obstetrics, abdominal and urinary pressure for diagnosis of disorders, and the like. In some such applications, it is desirable to measure pressure with an extremely small sensor so as not to disturb the system being monitored. For example, cardiovascular catheterization has become a major and common diagnositic tool in dealing with the cardiovascular system. In angioplasty (balloon pumping) to treat occlusions in the coronary artery of the heart, there is presently no satisfactory means of judging the results on-line, that is, as treatment is being administered. Existing catheter-tip pressure sensor are single-point, not highly reliable, very expensive, and too large for use within the coronary artery. Also, they typically offer only low-level output signals which are very susceptible to noise and artifact.

Recent advances in silicon micromachining technology have allowed to development of a wide range of solid-state pressure sensor. Amongst the most useful, on account of their increased sensitivity, are capacitive pressure sensors. In the past few years the use of impurity-sensitive etch-stops and deposited diaphragm structures have resulted in precise, ultrathin diaphragms that have substantially broadened the range of practical structures which can be realized. In particular, a significant miniaturization of solid-state pressure sensors is now feasible. See for example, H. Guckel, et al, "Laser-Recrystallized Piezoresistive Micro-Diaphragm Sensor," Dig. Tech. Papers, IEEE Int. Conf. Solid-State Sensors and Actuators, pp. 182–185 (June 1985).; R. S. Hijab and R. S. Muller, "Micro-mechanical Thin-Film Cavity Structures for Low Pressure and Acoustic Transducer Applications," Dig. Tech. Papers, IEEE Int. Conf. Solid-State Sensors and Actuators, pp. 178–181 (June 1985).; and S. Sugiyama, et al, "Micro-Diaphragm Pressure Sensor," IEDM Tech. Dig., December 1986. For a general review of factors affecting performance and down-sizing of pressure sensor, see H. L. Chau and K. D. Wise, "Scaling Limits in Batch-Fabricated Silicon Pressure Sensors," IEEE Trans. Electron Devices, Vol. ED-34, April 1987. Thus, some techniques are now known for fabricating thin diaphragms essential for the ultraminiature sensors. However, improved fabrication techniques are needed along with improved sensor packaging and interface electronics in order to allow the sensors to be scaled downwardly while maintaining high performance and high yield. The most commonly used techniques for forming a diaphragm and supporting rim structure from a silicon wafer involve anisotropically etching a recess for the reference cavity of the transducer on the front side a silicon wafer, and selectively etching away 90% or more of the back of the silicon wafer in order to form a diaphragm of desired thickness. The diaphragm thickness is typically controlled using a boron buried layer or a p-n junction etch-stop. This back etching is done normally with preferential etchants which give a bevel having a wall angle of about 52 degrees. Due to the thickness of the silicon wafer, much lateral area around the diaphragm of the transducer is required, thus making it difficult to produce a small device. This use of lateral space is not productive, in that it is not a functional part of the sensor.

Many solid-state pressure tranducers or sensors are made using a silicon wafer which is first preferably etched, and then electrostatically bonded to a glass substrate. In many such sensors, particularly those having larger diaphragms, the electrostatic bonding process requires the application of a very high applied field which tends to pull the diaphragm over the glass and weld it to the glass, thus resulting in an inoperable device. To avoid this problem, a field shield plate, which can be one of the electrodes of the capacitive transducer, is grounded during the sealing processing. However, grounding of individual capacitor plates during a batch process is very hard to arrange, and is more effectively done only when the transducers are bonded to a supporting piece of glass one at a time. However, to produce commercial quantities of transducers, it is highly desirable to be able to seal an entire wafer of silicon transducers to a glass plate at one time without having to ground the individual capacitor plates of the transducers.

Another problem with many techniques used for producing solid-state pressure sensors is that numerous processing steps are required, including a number of steps requiring critical alignment and masks and the like, thus increasing costs and reducing yield. Thus, it would desirable to provide for a simpler, more reliable process requiring fewer processing steps and fewer critical alignment steps. In this regard, it is noted that existing techniques for making ultraminiature pressure sensors are typically costly. For example for sensors approaching one millimeter in diameter, devices may cost as much as several hundred dollars each. Clearly, it would very desirable to provide a pressure sensor structure and method of making it which would permit the cost of producing such ultraminiature devices to be reduced considerably, perhaps by as much as an order of magnitude or more.

In light of the foregoing, it is a primary object of the present invention to provide an improved solid-state pressure sensor structure and method of making it which allows ultraminiature pressure sensors to be fabricated with fewer, less costly steps and greater yield. Other objects of the present invention include eliminating the large rim areas associated with existing pressure sensors having a diaphragm and rim structure made from bulk silicon, and eliminating the need to provide a field shield plate during the electrostatic bonding process.

Other objects of the present invention include providing a pressure sensor that is capable of multipoint operation, is addressable, and is compatible for use on a multisite catheter having only two leads, namely the electrical power supply leads. One more object is to provide such a sensor which allows on-chip temperature measurement for purposes of compensation. Yet another object is to provide such a catheter system suitable for medical uses such as cardiovascular catheterization. Additional objects of the invention include providing a transducer fabrication process that is fully batch in nature and does not require individual handling of small parts.

SUMMARY OF THE INVENTION

In light of the foregoing problems and to fulfill one or more of the foregoing objects, the present invention provides an ultraminiature capacitive pressure sensor having a silicon diaphragm and rim structure made with a simple double-diffusion process. This novel diaphragm and rim structure is part of a silicon transducer chip which is electrostatically bonded to a glass support plate prior to removal of all of the wafer except for the diaphragm and rim structure. The novel diaphragm and rim structure features a very small rim area, thus allowing the transducer to be constructed in ultraminiature form. Thus, capacitive pressure sensor of the present invention can be mounted, for example, in a 0.5 millimeter OD multisite cardiac catheter suitable for measuring blood pressure gradients inside the coronary artery of the heart. The silicon pressure transducer preferably includes supporting interface circuitry on a chip fastened to the same glass support plate as the diaphragm and rim structure.

According to one aspect of the invention, there is provided a method of making a pressure sensor having a diaphragm in rim structure including bulk silicon, which comprising the steps: (a) providing a silicon wafer; (b) forming at least one mesa upon the silicon wafer to be used as part of the rim structure of the pressure sensor; (c) impregnating a selected portion of the silicon wafer which includes the mesa with at least a first material which alters an etching characteristic of the first selected portion; (d) impregnating a second selected portion of the silicon wafer which will become the diaphragm of the sensor with a second material which alters an etching characteristic of the second selected portion; and (e) removing by etching at least a selected third portion of the silicon wafer adjacent to the first and second portions as part of forming the diaphragm and rim structure. Steps (c) and (d) are preferably performed by a deep diffusion and a shallow diffusion respectively of an impurity dopant, namely boron, into the silicon wafer.

According to a second aspect of the invention, there is provided an ultraminiature solid-state capacitive pressure transducer, comprising: an integrally formed structure made from single-crystal material and having a diaphragm and a rim extending about a substantial portion of the periphery of the diaphragm, the structure having at least two dimensions orthogonal to one another of less than one millimeter. The transducer typically includes a glass plate that is electrostatically bonded to at least part of the rim structure, and the single-crystal material is typically a silicon. The rim and diaphragm and heavily impregnated with at least a first material which alter an etching characteristic of the rim and diaphragm in comparison to single-crystal material which contains substantially less of such first material. The first material is typically a impurity dopant selected from a group of dopants including n-type materials and p-type materials, with the preferred p-type material being boron.

According to a third aspect of the present invention, there is provided a multipoint pressure-measuring catheter system, comprising: a catheter; a plurality of pressure sensors spaced along the catheter; and single conduit means within the catheter for providing a path for signals to be passed between an external monitor and each of the pressure sensors. The pressure sensors each include pressure transducer means for converting a sensed pressure into an internal signal, switching means for applying the internal signal to the signal conduit means, and addressing means responsive to a command signal from the external monitor for selectively interrupting switching means, whereby the external monitor may receive separately the internal signal generated by each of the pressure sensors.

These and other aspects, objects and advantages of the present invention will be better understood by reading the following detailed description in conjunction with the accompanying drawings and appended claims.

BRIEF DESCRIPTION OF THE DRAWINGS

The drawings form an integral part of the description of the preferred embodiments and are to read in conjunction therewith. Like reference numerals designate components in the different Figures, where.

DETAILED DESCRIPTION OF THE PREFERRED EMBODIMENTS

Figure 1:
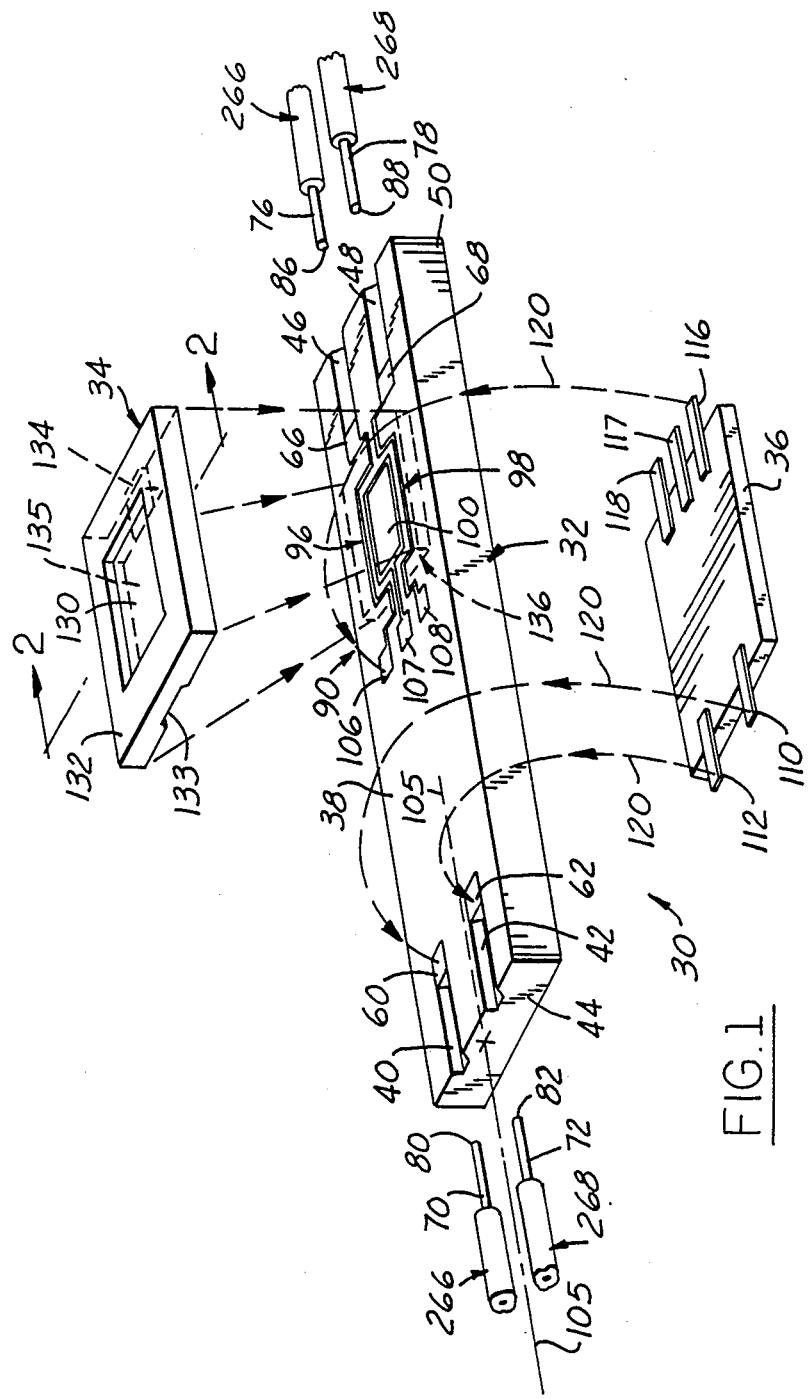
FIG. 1 is an exploded perspective view of an ultraminiature capacitive pressure sensor of the present invention which includes a silicon pressure transducer and integrated circuit chip mounted on a glass substrate.

Referring to FIG. 1, an ultraminiature pressure sensor 30 of the present invention is shown in an exploded perspective view for ease of understanding. The pressure sensor 30 is comprised of three main components: a patterned glass support substrate 32 selectively metallized in certain areas, a patterned silicon transducer chip 34, and an interface circuit chip 36. The glass substrate has formed two therein grooves 40 and 42 at the left end 44 of the glass substrate 32, and a second pair of grooves 46 and 48 at the right end 50 of the glass substrate. Formed just beyond the inner end of the groove 40 and 42 are metallized bonding pads 60 and 62. Similarly, just beyond the inner ends of grooves 46 and 48 are metallized bonding pads 66 and 68. Typically, the grooves have a trapezoidal cross-section. The grooves 40, 42, 46 and 48 are metallized and are electrically connected respectively to pads 60, 62, 66 and 68. The grooves 40 and 42 receive wires 70 and 72, while grooves 46 and 48 receive wires 76 and 78. The wires 80, 82, 86 and 88 are respectively soldered or otherwise secured to grooves 40, 42, 46 and 48 prior to using the pressure sensor 30, as will later be described.

Upon the top surface 38 of the glass substrate 32 is a patterned metallized area or region 90 containing a first (rear) and second (front) interconnect traces 96 and 98, which follow the periphery of and are spaced from a metallized rectangular pad 100 which serves as one-half of the active capacitor $C_X$ of the pressure transducer of sensor 30 namely the lower plate of capacitor $C_X$. In region 90 are three metallized pads 106, 107 and 108 spaced apart from one another in a line perpendicular to the central longitudinal axis 105 of the glass support substrate 32. The first interconnect trace 96 is connected at one end thereof to pad 106, and at the other end thereof to pad 66. The second trace 98 is connected at one end thereof to pad 108 and at the other end thereof to pad 68. An enlarged view of the traces 96 and 98 and capacitor 100 is provided in FIG. 3. The circuit chip 36 contains a first set of beam leads 110 and 112, at the left and thereof, and a second set of beam leads 116, 117 and 118 at the right end thereof. As indicated by dashed lines 120, the circuit chip 36 is assembled to the glass support substrate 32 by flipping chip 36 over so that the beam leads 110, 112, 116, 117 and 118 respectively about against and may be bonded to bonding pads 60, 62, 106, 107 and 108 by ultrasonic bonding or thermocompression.

The patterned transducer chip 34 is preferably made from a conventional single crystal silicon wafer of the type widely used in the semiconductor industry. The chip 34 contains a very thin centrally located diaphragm 130 which is integrally connected to an surrounded by a much thicker rectangular rim 132. The rim 132 is preferably formed with at least two reference pressure inlet channels 133 and 134 respectively located on opposite sides of the rim, and which (until sealed off) provide access to a small space or chamber 135 under diaphragm 130. The silicon transducer chip 34 is electrostatically bonded to the glass substrate 32 in the location indicated in phantom by-dotted lines 136. The circuit chip 36 preferably contains all of the necessary read-out electronics, as will be further explained.

Key parts of the structure and process for making the pressure sensor 30 are the structure and process for making the transducer chip 34, and the process for joining of this chip to the glass substrate 32. This process and the resulting structure is illustrated in FIGS. 1 through 4.

The fabrication process starts with a 250 micron thick borosilicate glass plate 138 which may be a Corning 7740 glass plate, and which becomes the patterned glass plate 32 after processing. Since the height of the gap between the metallized capacitor plate 100 and silicon diaphragm 130 shown in FIG. 1 is typically less than 5 microns, a very smooth finish on both plates 100 and 140 are important in achieving high yield. Grooves 40, 42, 46 and 48 are first etched into the glass plate 32 with concentrated hydrofluoric (HF) acid using a gold/chromium mask. The gold/chromium mask is preferably formed in two layers by vacuum evaporation, with the chromium layer being about 200 to 400 angstroms thick and eing deposited first, and the gold layer being about 3,000 to 5,000 angstroms thick. This mask is patterned using conventional photolithographic techniques so that the HF acid isotropically attacks the glass only in the area where the grooves are desired. Once the grooves are formed, the two layer mask is completely removed and a second multiple-layer conductive coating is deposited everywhere on the glass, and photolithographically patterned to form the appropriate metallized areas, namely grooves 40, 42, 46 and 48, bonding pads 60, 62, 66 and 68, interconnects 96 and 98 the lower plate 100 of the active capacitor (i.e., the transducer capacitor), and the metal pads 106, 107 and 108. Using batch processes, sites for numerous identical sensors 30 are created on a single sheet of glass 138.

Figure 3:
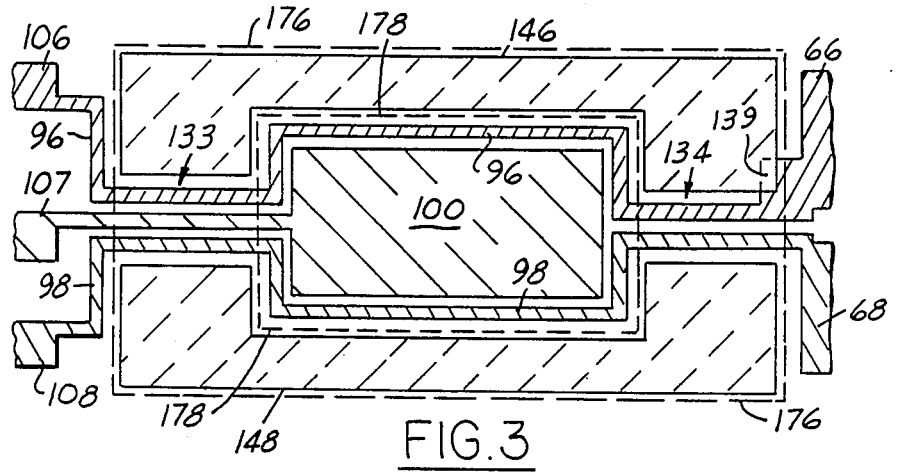
FIG. 3 is a top cross-sectional view of the silicon pressure transducer of FIG. 1 after it is bonded to the glass substrate.

The multiple-layer conductive coatoing may be made of a first layer of chromium about 300 angstroms thick for good adhesion to the glass substrate 32, and a second layer of gold about 2000 to 4000 angstroms thick for making good electrical contact with the wires, beam leads and the like connected thereto. Alternatively, a combination of three metal layers consisting of a first layer of titanium, a second layer of platinum, and third or top layer of gold could be used as the conductive coating. In this alternative conductive coating, the titanium and platinum layers should have a combined thickness of about 200 to 300 angstroms, while the gold layer should have a thickness of 2000 to 4000 angstroms. As is shown in FIG. 3, an area of overlap 139 between the rim 132 and the interconnect trace 96 in the vicinity of the metal pad 66 provides the electrical connection between the rim 132 and trace 96. The rim 132 serves as the conductive path leading to the top plate of the transducer capacitor, namely the silicon diaphragm 130.

Referring to the various views of FIG. 2, the processing of the silicon transducer chip 34 will now be explained. Starting with either n-type or p-type 100-oriented silicon wafer having a resistivity of about 6–8 ohm-centimeters, the wafer 140 is first cleaned. The wafer 140 is next thermally oxidized to a thickness of about 0.5 microns on all surfaces as indicated by a top layer 142 and bottom layer 144 of silicon dioxide in FIG. 2A. The wafer 140 is then coated with a layer of photoresist, which is then patterned in accordance with a first mask so as to leave resist in two flattened U sections 146 and 148 shown in FIG. 3, with cross-sectional portions of sections 146 and 148 thereof being shown in FIG. 2A. The wafers are aligned in a mask aligner so that the 110-orientation flat is parallel to the long side of the diaphragm 100. The silicon dioxide of top layer 142 is then patterned, and undesired areas thereof removed, leaving $SiO_2$ portions 152 and 154 located under the remaining photoresist portions 146 and 148. The photoresist portion 146 and 148 are then removed.

Figure 2A:
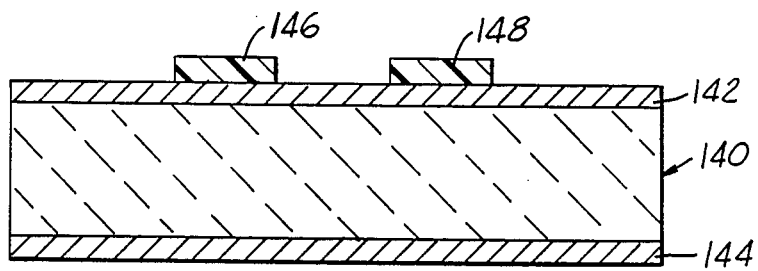
FIGS. 2A-2H are a series of cross-sectional side views taken along ine 2—2 of FIG. 1 showing the various processing steps associated with fabricating the silicon transducer from a silicon wafer, and bonding it to the glass substrate.
Figure 2B:
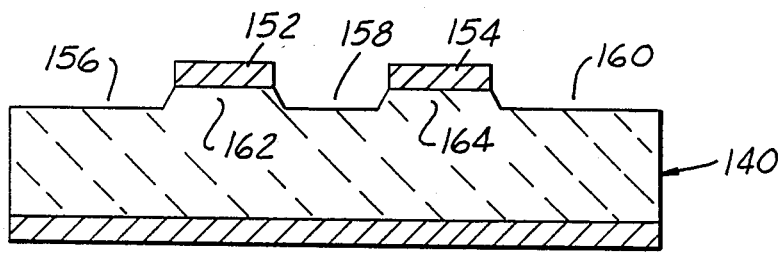
Figure 2C:
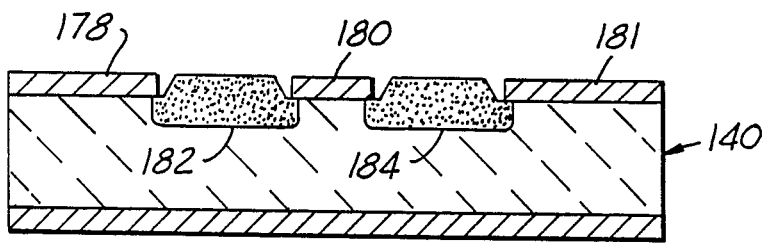

Next as shown in FIG. 2B, the shallow recessed sections 156, 158 and 160 are removed by etching the top of the silicon wafer 140 using potassium hydroxide as an etchant and the silicon dioxide portions 152 and 154 as a mask. The recesses 156–160 have positioned therebetween unetched mesas 162 and 164 respectively located under silicon dioxide portions 152 and 154. The recesses 156 and 160 provide the horizontal spacing between adjacent transducers, while the recess 158 forms the gap which become space 135 in the transducer capacitor. Next, the silicon dioxide portions 152 and 154 are etched away with buffered HF acid. Thereafter, a new layer of silicon dioxide is thermally grown to a thickness of about 1.2 microns and conforms to the existing mesa structure shape. It is then photolithography patterned in accordance with a second mask whose geometry is depicted in FIG. 3 by large and small rectangles 176 and 178 shown in dashed lines. After this patterning, as shown in FIG. 2C, the silicon dioxide portions 178, 180 and 181 remain.

Referring again to FIG. 2C, the silicon wafer 140 is then impregnated in selected areas with etch-rate altering impurities by performing a deep boron diffusion, using the oxide mask portions 178, 180 and 181 to prevent the dopant gas from diffusing too far thereunder. This deep boron diffusion step defines the intended rim areas, such as rim portions 182 and 184. The deep boron diffusion is preferably performed at 1175 degrees C. for 15 hours using a solid dopant source (e.b., boron nitride) to provide a desired rim thickness as will be further explained. The doped wafer is then placed in a drive-in furnace at about 1100 degrees C. for 40 minutes to re-oxidize the surface boron-glass layer created during the previous step to a thickness of about 0.5 microns, as indicated by layer 188 of FIG. 2D.

Figure 2D:
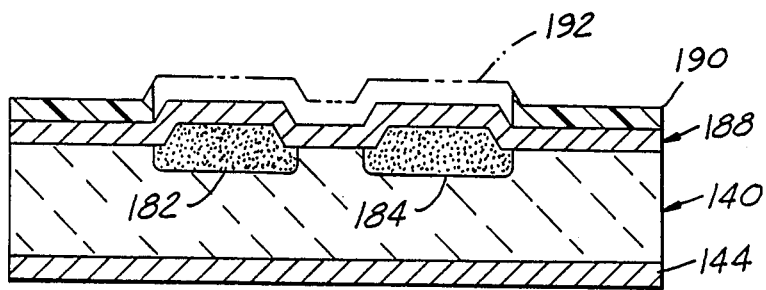

Thereafter, as shown in FIG. 2D, a layer 190 of photoresist is deposited over the new oxide layer and patterned by removing all portions of the photoresist in the entire transducer area 192, i.e., the area within the large rectangle 176 indicated by dashed lines in FIG. 3. Thereafter, the silicon dioxide in the transducer area 192 is removed, thus leaving oxide layer portions 196 and 198 shown in FIG. 2E.

Figure 2E:
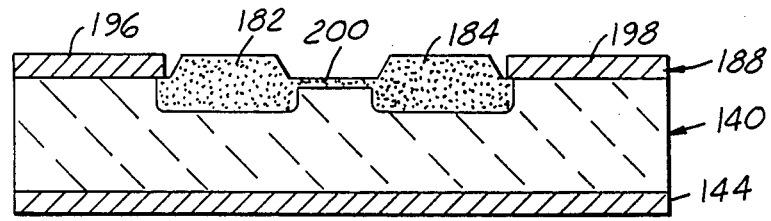

Next, as indicated in FIG. 2E, a short or shallow boron diffusion step is performed in the open transducer area within rectangle 176, including in the central region 200 between rim areas 182 and 184. The depth of this short boron diffusion is equal to the desired thickness for the silicon diaphragm 136. For a thickness of 2 microns, for example, the short boron diffusion step is performed at 1175 degrees Centrigrade for 30 minutes.

Figure 2F:
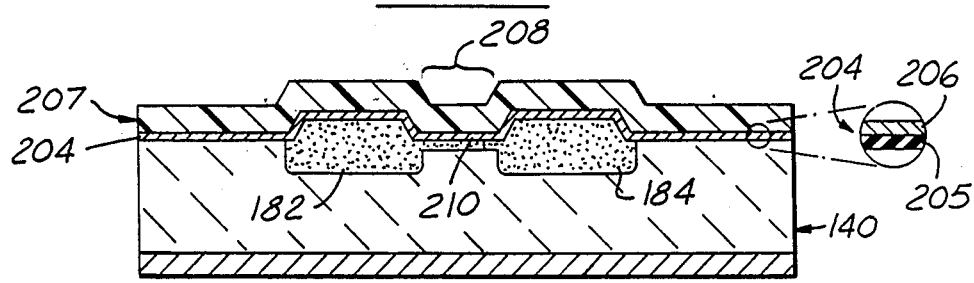
Figure 2G:
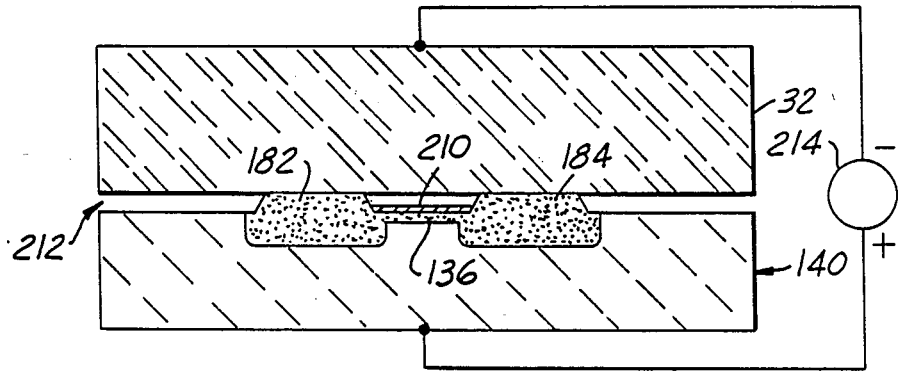

Thereafter, if desired, the diaphragm area 136 may be covered with a dielectric layer for protection against electrical shorts and environmental contamination. The dielectric layer 204 is preferably a compound layer comprised of a first sublayer 205 of thermally grown oxide 1000 angstroms thick and a second sublayer 206 of of CVD silicon nitride ($Si_3N_4$) 1000 angstroms thick. The resulting composite layer 204 is nearly neutral in stress (or in mild tension). By altering the thickness of its sublayers, such a composite layer 204 can be readily adjusted to have a temperature coefficient closely matching that of the underlining silicon diaphragm 136. The dielectric layer 204 is initially grown and deposited over the entire wafer 140, as indicated in FIG. 2F. Next, the dielectric layer 204 is removed over all areas, other than the diaphragm 136. This is done as follows. A layer 207 of photoresist is applied and patterned using a fourth mask having a geometry corresponding to the inside rectangle 178 shown in FIG. 3, so that a patterned photoresist portion 208 remains and covers the diaphragm area. Then, using a plasma (dry) etch of silicon nitride, followed by a buffered HF (wet) etch to remove the oxide layer, the dielectric layer 204 is removed from all areas of wafer 140 other than the diaphragm 136, so that only dielectric layer portion 210 remains, as best seen in FIG. 2G. The same buffered HF etch also removes the back side oxide layer 144.

Thereafter, a bonding step is performed, as illustrated in FIG. 2G, wherein the silicon wafer 140 is batch bonded to the glass plate 32 using an electrostatic (anodic) bonding technique. The alignment of the silicon wafer 140 to the glass substrate 32 is straightforward since the glass is transparent. The bonding is preferably formed by heating the assembly 212 of the wafer 140 and glass substrate 32 to between 400 and 450 degrees C., and then applying 400 to 600 volts DC from a suitable source 214 across the glass plate 32 and silicon wafer 140 for two minutes. This forms a hermetic seal between the rim structure (e.g., rim portions 182 and 184) of the wafer 140 and the glass 32. The electrostatic bonding of a silicon wafer to glass is widely used to construct other types of silicon capacitive pressure transducers. See for example, Y. S. Lee and K. D. Wise, "A Batch-Fabricated Silicon Capacitive Pressure Transducer With Low Temperature Sensitivity", IEEE Transactions on Electron Devices, Vol. ED-29, No. 1, pp. 42–48 (January 1982), which is hereby incorporated by reference. Thus, the electrostatic bonding step need not be further described here.

Figure 2H:
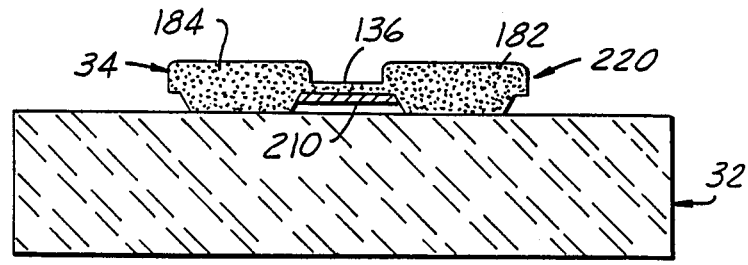

Following the bonding step, the silicon wafer glass assembly shown in FIG. 2G is immersed in an anistropic etchant for silicon (such as ethylene-diamine/pyrocatechol/water (EDP)) and all of the silicon wafer 140 is dissolved, except for the boron doped rim portions of the wafer, such as rim portions 182 and 184, and diaphragm 136 therebetween. Thus, only the boron-doped portions of the wafer 140 are retained, and these portions constitute the patterned transducer chip 34 shown in FIG. 1. These portions do not etch in EDP, nor do the interconnect metals, the glass, or the oxide or other dielectric layers. The result of this etching operation is a glass plate 32 containing a glass-silicon transducer 220 as shown in FIG. 2H.

Figure 4:
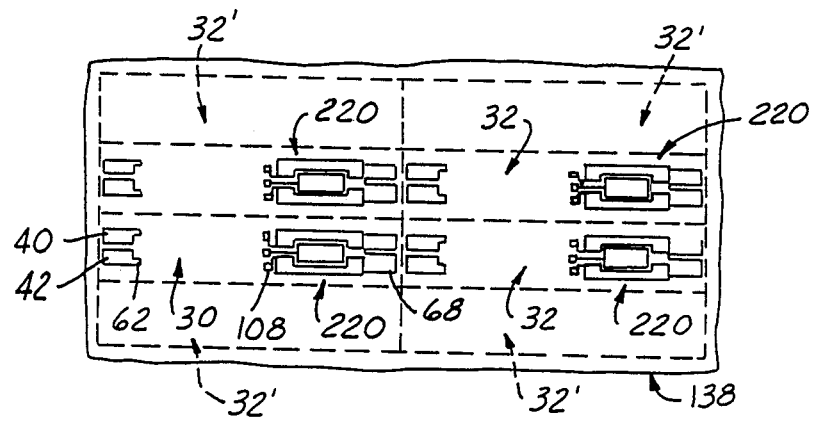
FIG. 4 is a plan view showing several completed glass silicon transducers from a matrix array of such chips which have been simultaneously bonded to a glass plate using the batch processing steps of FIG. 2, prior to dicing the plate into individual sensors.

FIG. 4 shows a portion of a glass substrate 138 having eight glass substrates 32 prior to being diced into individual substrates. The four substrates 32 in the center are shown with completed glass-silicon transducers 220 of the type shown in FIG. 2H. (To avoid cluttering the Figure, the glass substrates 32' are shown without their transducers 220.) As can be readily appreciated by those skilled in the art, the fabrication process described with respect to FIGS. 1–3 is fully compatible with automated batch processing techniques which will allow the transducers 220 to be prepared en masse, that is by the hundreds (or more) from a single silicon wafer. The glass substrates 32 shown in FIG. 4 are diced along the vertical and horizontal dashed lines 222 and 224 to separate them into individual substrates 32.

As should be evident from the foregoing, the transducer process described above utilizes single-sided processing of silicon wafers having normal thickness. It requires only three non-critical masking steps to produce the patterned silicon wafer diaphragm and rim structure or chip 34, and produces a very high yield. (If the optional dielectric $SiO_2$—$Si_3N_4$ layer is used, then a fourth mask is required.) The rim and diaphragm thicknesses are set by the deep and shallow boron diffusion steps with a precision of better than 0.1 microns, while lateral dimensions are controlled by lithography to a precision of better than 0.25 microns.

The rim size is scalable, but is typically 12 microns thick and 80 microns wide. This is significantly smaller than those found in conventional pressure sensing structures, in which the diaphragm is formed from a back side anisotropic etch, and the width of the rim is comparable to the wafer thickness (300 microns or more). Furthermore, in the present approach, batch wafer bonding to the glass before wafer dissolution eliminates handling of individual diaphragm structures until die separation and final packaging. The glass 138 may be sawed into individual dies (i.e., glass plates 32) before or after the bonding of the chips 36 to the metal pads 60, 62, 106, 107 and 108.

Figure 5:
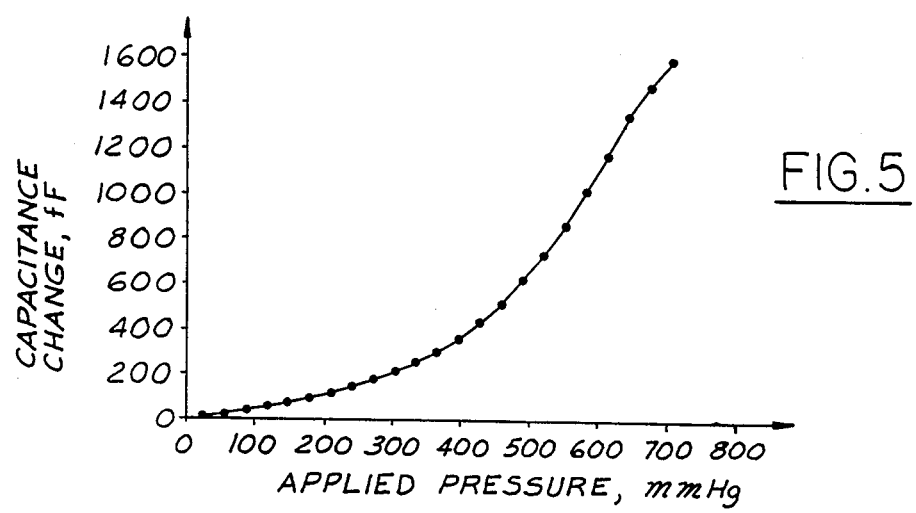
FIG. 5 is a graph showing the capacitance change versus applied pressure characteristics of one ultraminiature pressure sensor constructed in accordance with the present invention.

FIG. 5 shows the measured pressure characteristics of the ultraminiature sensor illustrated in FIG. 1. The reference cavity 135 for the sensor 130 upon which the measurements were made was sealed and at atmospheric pressure. However, differential pressure measurement with an unsealed reference pressure inlet channel 134 is also possible with the transducer 220. The sensor 30 upon which the measurements shown in FIG. 4 were made had a diaphragm size of 260 microns $\times$ 600 microns $\times$ 2 microns, a capacitor plate separation of 2.2 microns, a zero-pressure capacitance of 0.33 pF, a pressure range of about 500 mmHg and a pressure sensitivity of 1440 ppm/mmHg. By scaling lateral and vertical diaphragm dimensions, the pressure sensitivity of the transducer 220 can be scaled over several orders of magnitude.

Figure 6:
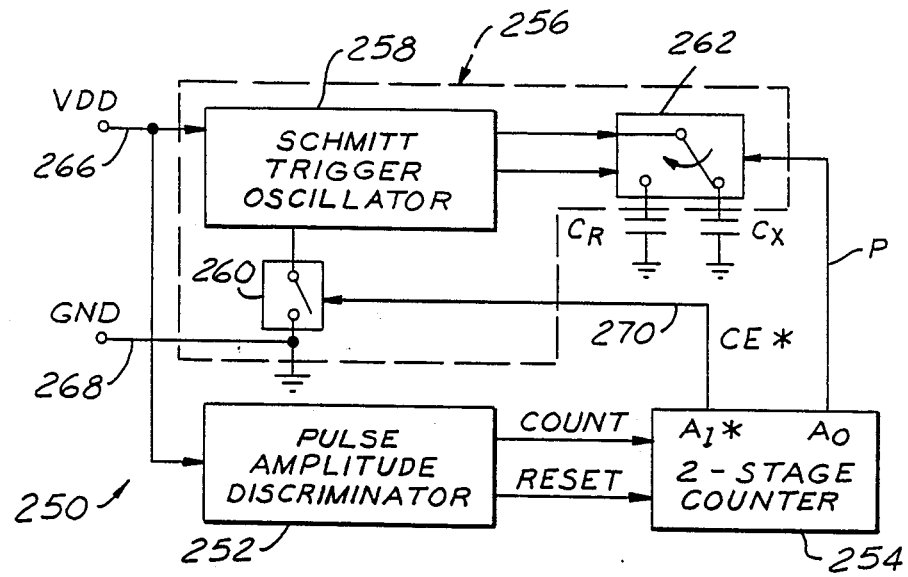
FIG. 6 is a functional block diagram of a preferred embodiment for the on-chip circuitry used in the FIG. 1 pressure sensor.

The small size of the capacitance change associated with the sensor and the need to simplify packaging by minimizing external leads poses a challenge to the design of the circuit chip. An oscillatory-type circuit which requires only two external leads has been developed in which the supply current is pulse-period modulated by the applied pressure. A functional block diagram of this circuit is shown in FIG. 6. The circuit 250 includes a pulse amplitude discriminator circuit 252, a two-stage counter 254, and a Schmitt trigger oscillator circuit 256 including a Schmitt trigger oscillator 258, an enable switch 260, and a two-position selector 262. Electrical power and signal communication is delivered over conductors 266 and 268 which respectively are nominally at a solid-state circuit supply voltage VDD (such as +5 VDC) and ground potential GND (0.0 volts). The operation of circuit 250 may be explained in brief as follows. Schmitt trigger oscillator 258, in which the period of oscillation is dominated by the charging time of the transducer capacitance $C_X$, sets up an oscillation in the supply current delivered via conductors 266 and 268. The electrical pressure signal originating with capacitor $C_x$ is then extracted by detecting the frequency of current variations over the power lines 266 and 268. Tradeoff between pressure signal bandwidth and resolution can be attained by altering the length of the sampling time. Temperature compensation is accomplished by differencing the oscillation period produced using the transducer with that of an on-chip reference capacitor $C_R$ which may be a thin film capacitor integrally fabricated with the other circuit components on circuit 250 in IC chip 36. The reference capacitor $C_R$, together with the temperature coefficient of the circuit supplying power to capacitor $C_R$, also serves as a transducer for on-chip temperature readout. Site and pressure/temperature transducer addressing is accomplished by signaling over the supply line 266 to circuit 252, which triggers an on-chip counter 254 and allows one particular sensor on a bussed multisensor line to be activated, while inactivated oscillator circuits such as circuit 256 are disabled. Thus multisite operation is possible. By depositing a thin film metal resistor having a high temperature coefficient of resistance on the diaphragm 130, it is possible to measure dynamic changes in temperature as well as pressure at each sensing site to allow future thermal dilution measurements of blood flow.

The addressable read-out circuit 250 in FIG. 5 may be fabricated on a single integrated chip such as chip 36 shown in FIG. 1. Prototypes of the chip 36 have been fabricated using standard NMOS processing, with beam leads to allow low-capacitance low-profile high-density interconnects to the transducer 220 and output leads 60, 62, 66 and 68 via the glass substrate 32. Use of a hybrid arrangement, as shown in FIG. 1 where the IC chip 36 and pressure transducer 200 are separately fabricated and then connected together, has several important advantages: (1) the circuits 250 can be processed using standard IC fabrication techniques and may be realized using a chip foundry; (2) the circuitry 250 is not exposed to the high voltage needed for the electrostatic bonding process; and (3) working circuit chips 36 can be selected for bonding to transducers 220, thus improving yield.

Figure 7:
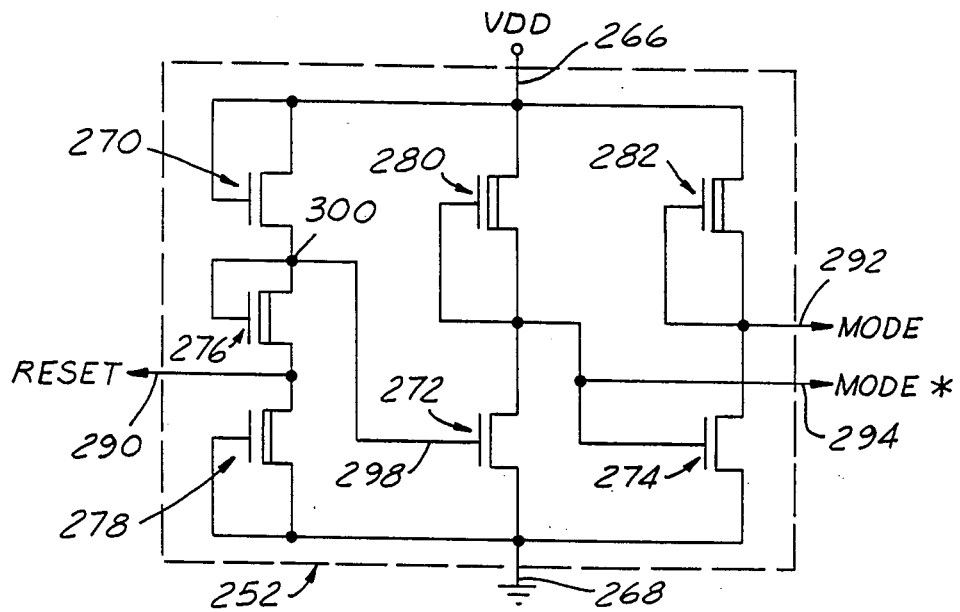
FIG. 7 is a circuit diagram of the pulse amplitude discriminator module of FIG. 6.
Figure 10:
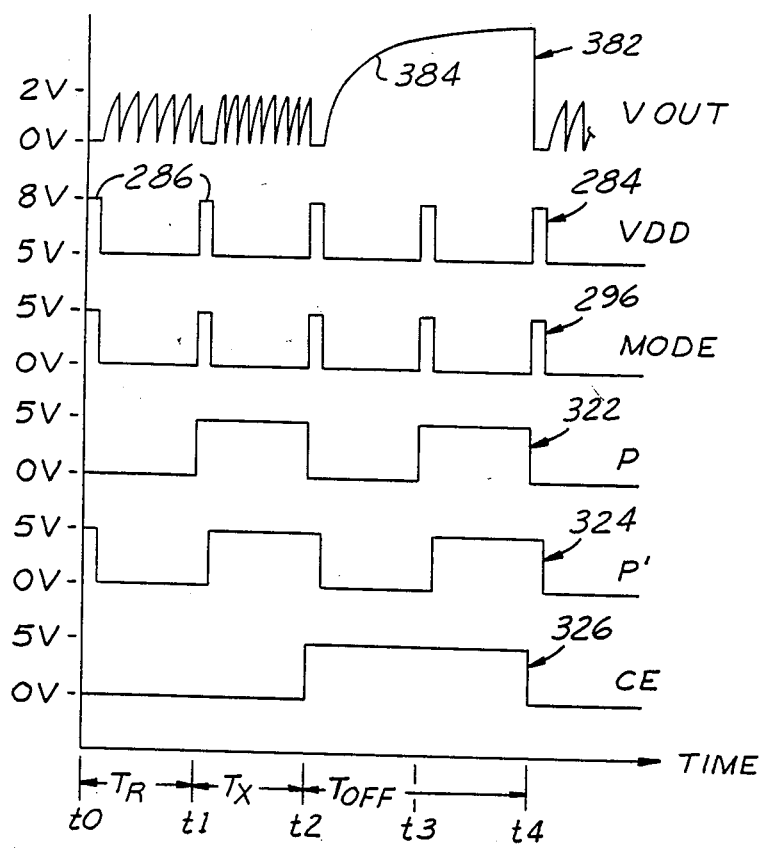
FIG. 10 is a signal timing diagram showing waveforms and timing relationships of various signals in the circuitry illustrated in FIGS. 6-10.

FIG. 7 shows a detailed circuit diagram of the pulse amplitude discriminator circuit 252. The circuit 252 contains seven metal-oxide-semiconductor (MOS) insulated-gate field effect transistors (FETs) 270 through 282. FETs 270-274 are enhancement-mode devices, while FETs 276-282 are depletion-mode devices. The circuit 252 receives power over supply lines 266 and 268, and receives two different types of commands over supply lines 266. The nominal voltage VDD is +5 volts DC. The first command signal is a clock signal which is delivered at +8 volts DC. The second command signal is a reset signal which is delivered at +11 volts DC. The first command signal is shown in FIG. 10 on waveform 284. The pulses 286 are the clock pulses. The circuit 252 produces three outputs signals, namely the RESET on line 290 and the MODE and MODE* signals on lines 292 and 294. A waveform 296 in FIG. 10 shows the timing and voltage levels of the MODE signal. The MODE* signal is the complement of the MODE signal. (The asterisk symbol is used to indicate the complement of whatever signal it follows.) The operation of circuit 252 in FIG. 7 may be briefly explained as follows. When VDD line 266 temporarily goes to 8 volts, it draws node 300 to a sufficiently high level, causing gate 298 to transistor 272 to go high, which turns transistor 272 on. Accordingly, MODE* goes from a high to a low logic level, and transistor 274 turns off, which makes the MODE signal on line 292 switch from a low logic level to a high logic level. When VDD line 266 returns to 5 volts, gate 298 returns to a low logic level causing transistor 272 to turn off. Accordingly, the MODE* signal switches from a low to high logic level, and transistor 274 turns on, which causes the MODE signal on line 292 to switch from high to low. When the VDD line goes to 11 volts, indicating a RESET command, it draws reset line 290 from a low to high logic level.

Figure 8:
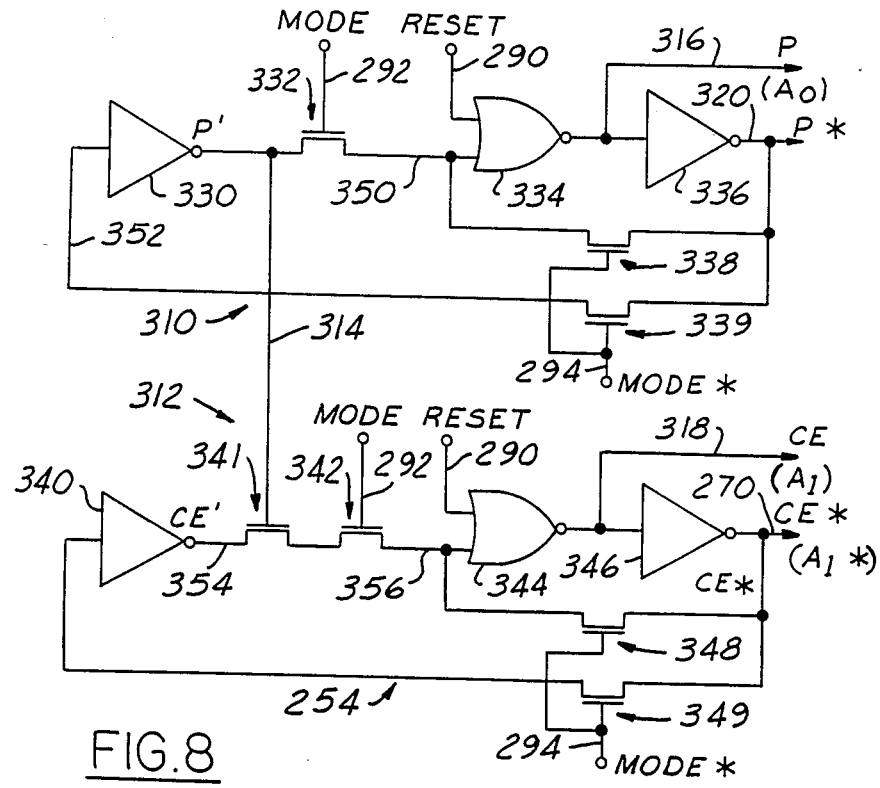
FIG. 8 is a circuit diagram of the two-stage counter of FIG. 6.

FIG. 8 is a circuit diagram of the two-stage counter circuit 254 shown in FIG. 6. The circuit 254 includes a first stage 310 and a second stage 312 interconnected by a single conductor 314. The output signal P on line 316 of first stage 310 is the low-order bit output of counter 254, while the output signal CE (which stands for Chip Enable) is the output for the high-order bit of counter 254. The first and second stages 310 and 312 each receive the MODE, MODE* and RESET signals respectively from lines 292, 294 and 290. The circuit 254 provides as outputs the P and P* signals on lines 316 and 320 respectively from the first stage 310, and provides as outputs the CE and CE* signals on lines 318 and 270 of the second stage 312. In the FIG 10 graph, waveforms 322, 324 and 326 show the timing relationships for signals P, P', and CE respectively.

As shown in FIG. 8 the first stage 310 includes inverter 330, MOSFET 332, NOR gate 334, inverter 336 and MOSFETs 338 and 339, all connected as shown. The second stage 312 includes: inverter 340, MOSFETs 341 and 342, NOR gate 344, inverter 346 and MOSFETs 348 and 349, all connected as shown. The operation of stages 310 and 312 will now be briefly explained, and it will be assumed that the RESET line 290 remains at a low logic level, which causes NOR gates 334 and 344 to each function as a simple inverter. As long as the MODE* signal remains high, the transistors 338 and 348 conduct. In stage 310, the NOR gate 334 and inverter 336 act as a latch to hold on the signal present on line 320 whenever transistor 338 is on and transistor 332 is off. Similarly, in stage 312, the NOR gate 344 and inverter 346 act as a latch whenever transistor 348 is on (that is, conducting) and transistor 341 or 342 is off. Returning now to first stage 310, assume line 314 (the P' signal) is low. When the mode signal arrives on line 292, transistor 332 turns on, causing line 350 to go low irrespective of its previous state, which causes line 316 to go high and line 320 to go low. While the MODE signal on line 292, the MODE* signal on line 294 is low and transistors 338 and 339 are off. When the MODE signal on line 292 goes low, transistors 338 and 339 turn on, thus latching in the low signal on line 320 and simultaneously supplying a low signal on line 352 going to the input of inverter 330. This causes the output of inverter 330 and line 314 to go high. However, since transistor 332 is now off, the high signal on line 314 is unable to propagate through to line 350 at this time. When the mode signal on line 292 goes high again, the high signal on line 314 propagates through to line 350, thus causing line 316 to go high and line 320 to go low. When the mode signal goes low again, the low state of line 320 is latched in via transistor 338. Thus, it will be appreciated that the output 316 and 320 of first stage 310 change state each time that the mode signal on line 292 goes high.

In contrast, the outputs 318 and 270 of the second stage 312 toggle, that is, change state, only with every second time that the MODE signal on line 292 goes high. This is because the stage 312 contains an additional transistor 341 which only allows the output signal CE* on line 270 to change state when the MODE signal on line 292 and the signal on line 314 from stage 310 are both high. In all other respects, the operation of stage 312 is the same as stage 310. Note that when the RESET signal on line 290 goes high, the outputs of NOR gates 334 and 344 are forced low irrespective of the state of input lines 350 and 356, thus causing both the P signal on line 316 and the CE signal on line 318 to go low. Transistors 338 and 348 if on will latch in this RESET output state.

Figure 9:
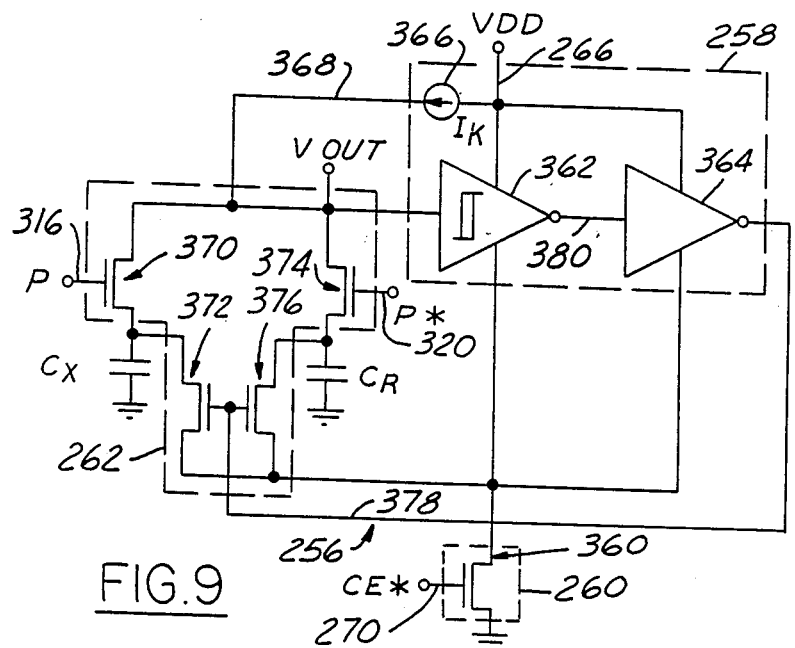
FIG. 9 is a detailed block diagram of the Schmitt trigger oscillator module of FIG. 6.

FIG. 9 shows a detailed block diagram of the trigger oscillator circuit 256 shown in FIG. 6. The circuit 256 includes a MOSFET 360, which acts as the enable switch 260. In the circuit 256 shown in FIG. 9, the switch 260 is turned on whenever the gate input line 270, containing the enable signal CE* from the second stage 312 of the counter 254 is high. In another circuit 256' (not shown), the input to transistor 360 would be the output signal CE on line 318 from the second stage 312 of counter 254. Since the enable switch 260 must be on in order for the oscillator circuit 256 to operate, it will be appreciated that the input signal to transistor 360 is effectively an address signal which must be high in order for the oscillator circuit 256 to be addressed. The Schmitt trigger oscillator 258 consists of three components, namely an inverting Schmitt trigger 362, inverter 364 and a source 366 of approximately constant current which is provided at a predetermined level from supply line 266 to output line 368. The current source 366 is set to produce the desired rate of charging of the transducer capacitor $C_X$ and the reference capacitor $C_R$ shown in FIG. 9. The switching circuit 262 includes four enhancement-mode MOSFETs 370–376. The operation of circuit 256 will now be briefly explained. When circuit is enabled by a high signal on the input of transistor 360, and the output of inverter 364 on line 378 is low, transistors 372 and 376 will be off, thus permitting capacitors $C_X$ and $C_R$ to charge. When signal P on line 316 is high, transistor 370 is on, thus allowing transducer capacitor $C_X$ to charge, and the reference capacitor $C_R$ will not charge since the complementary signal P* on line 320 will be low. Conversely, when the signal P* on line 320 is high, transistor 374 will be on, thus allowing reference capacitor $C_R$ to charge, while transistor 370 will be off, so that capacitor $C_X$ cannot charge. The rate at which the capacitor $C_X$ and $C_R$ charge is determined by the rate at which current is supplied to line 368 from the constant current source 366. When either capacitor $C_X$ or $C_R$ charges to a predetermined threshold voltage level which exceeds the input threshold voltage required to turn Schmitt trigger 362 on, output of Schmitt trigger 362 on line 380 goes low, which causes the output of inverter 364 on line 378 to go high. This turns on transistors 372 and 376, discharging both capacitors $C_X$ and $C_R$. The voltage on line 368 immediately approaches zero volts, thus resetting the Schmitt trigger 362 and allowing the output of inverter 364 to go low high, which turns off transistors 372 and 376. At this point, either capacitor $C_X$ or $C_R$ is allowed to begin charging again.

Waveform 382 in FIG. 10 illustrates the operation of the FIG. 9 circuit by showing the output voltage VOUT on line 368. As shown in FIG. 10, the time period $T_X$ between t1 and t2 represents the interval during which the transducer capacitor $C_X$ is being repetitively charged and discharged by circuit 256. Similarly, the time period $T_R$ between times t0 and t1 represents the interval of time during which the circuit 256 is charging and discharging the reference capacitor $C_R$. During the time period $T_{OFF}$ from times t2 to t4, the circuit 256 shown in FIG. 9 is disabled, thus allowing the voltage VOUT on line 368 to approach the value of voltage VDD on line 266 as shown by waveform portion 384 of waveform 382 in FIG. 10. Since the constant source 366 may be measured or otherwise calibrated at a known temperature, any change in the rate of charging of reference capacitor $C_R$ can be correlated with reasonable accuracy to changes in temperature of the integrated circuit chip 336 in which capacitor $C_R$ is located. Given the small size of the sensor 30, and the proximity of capacitor $C_R$ to the diaphragm 130, will be appreciated that $C_R$ provides a convenient and accurate method for determining the temperature of the pressure transducer of sensor 30, so that the pressure readings obtained from the charging time of transducer capacitor $C_X$ can be accurately compensated for temperature by an external monitoring system which examines the charging rates of capacitors $C_X$ and $C_R$. These charging rates are monitored by monitoring the frequency of the current signal drawn by circuit 252 over power supply lines 266 and 268. As is well understood by those in the art, the amount of pressure applied to the diaphragm 130 of pressure transducer 220 directly influences the capacitance value of capacitor $C_X$. For example, as pressure increases, the capacitance value increases. Since changes in the capacitance value of capacitor $C_X$ results in proportional changes in the charging time of capacitor $C_X$, the pressure being applied to the diaphragm 130 can be readily determined by monitoring the frequency of the current signal on power lines 256 and 268 when capacitor $C_X$ is allowed to charge by transistor 370 being on, and transistor 372 being off, as has been discussed with respect to FIG. 9.

As will be readily understood by those skilled in the art, the pressure transducer 220 of sensor 30 can be operated in several ways. For example, the pressure transducer 220 can be sealed at ambient pressure, or under vacuum conditions. If sealed at ambient pressure, epoxy or other suitable sealing materials can be deposited at the openings of both reference channels 133 and 134 (see FIGS. 1 and 3). One disadvantage of sealing gas in the cavity or chamber 135 of the pressure transducer 220 is that it results in a pressure transducer which has a high temperature coefficient on account of the pressure of the trapped gas naturally changing within sealed chamber 135 as the gas temperature changes. If the transducers 200 are to be sealed under vacuum conditions, this may be done en masse simultaneously while they are still on the glass plate 138 before the glass plate sections 32 are diced into individual glass plates, by depositing a dielectric material with sealing properties directionally through a shadow mask at the mouth or opening of each of the reference channels 134 and 135. This task can be carried out in a sputtering chamber using silicon dioxide (or the like) as the sealing material using a shadow mask which only has openings above the reference channels.

Figure 11:
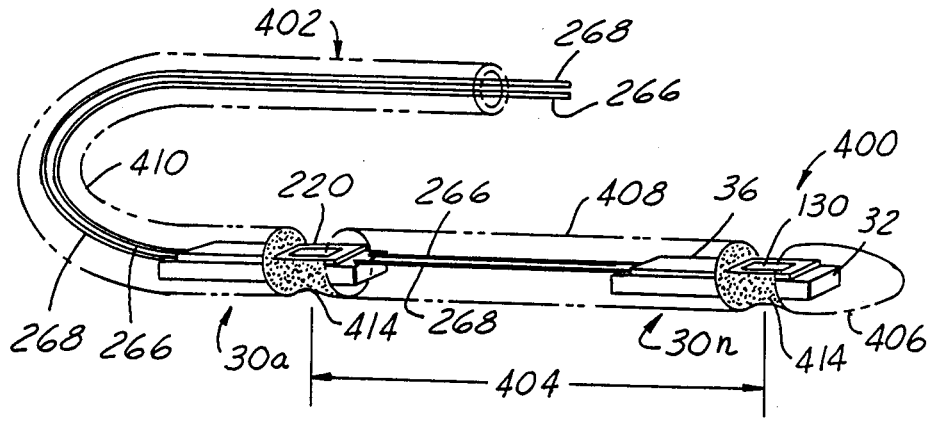
FIG. 11 is a multipoint pressure-sensing catheter system of the present invention which utilizes two of the FIG. 1 pressure sensors.

Referring now to FIG. 11, an ultraminiature catheter system 400 is shown. The system includes a very small catheter 402 such as 0.5 mm outer diameter (OD) tubing made from polyethylene or other suitable material, which has a length sufficient for the medical (or other) purpose to which the catheter will be placed. The system shown has two pressure sensors 30a and 30n, which are preferably constructed like sensor 30 shown in FIG. 1, spaced apart by a predetermined distance 404 such as 5 cm. The catheter 402 has three distinct sections: a catheter tip section 406, preferably round and gently pointed as shown to facilitate insertion into and passage along the interior of smaller blood vessels; an intermediate section 40 between the two pressure sensors 30a and 30b; and an extension section 410 to provide a conduit through which the wire leads 266 and 268 from electronic pressure sensor monitoring equipment may pass to reach the first and closest sensor 30a.

Preferably, the catheter system uses only the two wire leads 266 and 268 which are electrically connected in parallel to the two sensors 30a and 30n, while physically being arranged in series. Prior to the assembly of the catheter system 400 the pressure sensors 30a and 30n, which each include a glass plate 32 with the transducer chip 34 and read-out electronics chip 36 mounted thereon, is partially encapsulated with a biomedically compatible material 414 (i.e., one that is non-toxic and will not be adversely affected by the bodily fluids to which it be exposed) such as polyimide, silicone rubber, or the like, to seal off the hollow cylindrical interiors of the catheter sections from bodily fluids. The diaphragm 130 may have encapsulating material upon it, provided that the thickness of the layer of material upon the diaphragm is controlled so as to be at least about an order of magnitude more flexible than the silicon diaphragm 310. The integrated circuit chip 36 is preferably within the dry interior of the catheter section 408 (or section 410) where it will not be contacted by bodily fluids.

The required catheter leads 266 and 268 are attached via soldering or the like into the etched grooves 40, 42, 46 and 48 as has been explained in FIG. 1. Finally, the ends of the glass plates 32 are inserted in the catheter 402, leaving only the silicon diaphragms 130 exposed for measurement.

Prototypes of the above-described multipoint pressure-sensing catheter system have been fabricated and successfully tested. Table I below provides typical specifications for our prototypes.

TABLE 1

| | |
|---|---|
| Catheter Size | 0.5 mm OD |
| Diaphragm Size | 290 × 500 × 2 microns |
| Transducer Die Size | 0.45 × 1 mm |
| Circuit Die Size (Prototype) | 0.45 × 1.1 mm |
| Zero-Pressure Capacitance | 470 fF |
| Pressure Accuracy | 1 mmHg |
| Pressure Range | 500 mmHg |
| Signal Bandwidth | 50 Hz |
| Temperature Compensation | Frequency Differencing Using an On-Chip Reference Capacitor |
| Power Supply | Single 5 V |
| Signaling Levels | 8 Volts - Addressing, 11 Volts - Reset |
| Power Dissipation | less than 10 mW |
| Output Signal | Small-Signal Supply Current Variation (600 A p-p Over 850 microamps dc Baseline) |
| Number of Sensing Sites | 2 |
| Number of Transducers/Site | 2 (Pressure/On-Chip Temperature) |
| Number of External Leads | 2 |

It is recognized that those skilled in the art may make various modifications or additions to the preferred embodiments chosen to illustrate the invention without departing from the spirit and scope of the present contribution to the art. For example, the pressure transducers of the present invention may be made much larger or smaller than the embodiments described herein by appropriate scaling of various dimensions. Also, the pressure transducer of the present invention may be used to sense fluid flow and other conditions by providing appropriate means for causing deflection of the diaphragm are provided. Accordingly, it is to be understood that the protection sought and to be afforded hereby would be deemed to extend to the subject matter claimed and all equivalents thereof fairly within the scope of the invention.

We claim:

1. An ultraminiature solid-state capacitive pressure transducer which includes a parallel plate capacitor, comprising:

an integrally formed structure made from single-crystal material and having a diaphragm and a rim extending about a substantial portion of the periphery of the diaphragm, the structure having at least two dimensions orthogonal to one another of less than one millimeter, and the diaphragm constituting a plane supporting one plate of the parallel plate capacitor.

2. A transducers as in claim 1, further comprising:
a glass plate electrostatically bonded to at least part of the rim of the structure.

3. A transducer as in claim 1, wherein:
the single-crystal material is silicon, and
the rim and diaphragm are heavily impregnated with at least first material alters an etching characteristic thereof in comparison to single-crystal material which contains substantially less of such first material.

4. A transducer as in claim 3, wherein:
the first material is an impurity dopant selected from the group of dopants including n-type materials and p-type materials.

5. A transducer as in claim 3, wherein the first material is boron.

6. A transducer as in claim 1, wherein the rim and diaphragm are made from a common wafer of single-crystal material and the nominal width of the rim is at least three times smaller than the nominal thickness of the wafer from which it is made.

7. A transducer as in claim 6 wherein the nominal thickness of the rim is no more than about 80 microns, and the nominal height of the rim is no more than about 12 microns.

8. A transducer as in claim 1, wherein the nominal thickness of the single-crystal material of the diaphragm is no more than about two microns.

9. A transducer as in claim 1 having first and second electrically conductive parallel plates which form the parallel plate capacitor, whose capacitance is adjustable by a change in pressure upon at least one of the plates, further comprising an insulating nonflexible support substrate having an electrically conductive plate formed on a first side thereof, which constitutes the first parallel plate, and wherein:

the diaphragm of the integrally formed structure constitutes the second parallel plate,
the rim of the integrally formed structure is bonded to the first side of the support substrate and at least substantially surrounds the perimeter of the first parallel plate,
the nominal thickness of the rim is no more than about 80 microns and the nominal height of the rim is no more than about 12 microns, and
the nominal gap between the first and second parallel plates is less than five microns.

10. A transducer as in claim 9, wherein the overall size of the diaphragm measured in two orthogonal directions along the plane of the diaphragm is no more than about five hundred microns in each such direction.

11. A transducer as in claim 1, having first and second electrically conductive parallel plates which form the capacitor whose capacitance is adjustable by a change in pressure upon at least one of the plates, further comprising:

a thin composite dielectric layer formed on one side of the diaphragm; and
an insulating nonflexible support substrate having an electrically conductive plate formed on a first side thereof, which constitutes the first parallel plate, and wherein
the diaphragm of the integrally formed structure constitutes the second parallel plate,
the rim of the integrally formed structure is bonded to the first side of the support substrate and at least substantially surrounds the perimeter of the first parallel plate,
the composite dielectric layer is on the side of the diaphragm facing the first parallel plate, and is formed of at least first and second sublayers, the first sublayer including a thermally grown oxide and the second sublayer including a deposited silicon nitride.

12. A transducer as in claim 1, wherein the diaphragm of the integrally formed structure is rectangularly shaped, is centrally located in and surrounded by the rim, and has an average thickness which is at least a few times thinner than the average thickness of the rim.

13. A solid-state capacitive pressure transducer including a parallel plate capacitor therein, comprising:
an integrally formed structure made from single-crystal silicon semiconductor material and having a diaphragm and a rim that extends at least around a substantial portion of the periphery of the diaphragm, the diaphragm and rim being heavily impregnated with at least a first material which alters an etching characteristic thereof in comparison to single-crystal material which is identical to the heavily impregnated material of the diaphragm and rim except for containing substantially less of such first material, and wherein the diaphragm constitutes a supporting plane of one plate of the parallel plate capacitor.

14. A transducer as in claim 13, further comprising:
a glass plate electrostatically bonded to a generally flat surface of the rim, such that the diaphragm is generally parallel to and spaced closely to but remains apart from the glass plate.

15. A transducer as in claim 13, wherein the first material is an impurity dopant selected from the group of dopants including n-type materials and p-type materials.

16. A transducer as in claim 13, in which the transducer is part of a pressure sensor, further comprising:
an insulating plate bonded on one side thereof to at least part of the rim of the integrally formed structure, a thin electrically conductive pad located on the side of the insulating plate bonded to at least part of the rim, the conductive pad being spaced apart from and generally parallel to the diaphragm and forming a stationary plate of the capacitor of the transducer, with the diaphragm forming a flexible second plate of the capacitor.

17. A transducer including a pressure-adjustable parallel plate capacitor, comprising:
a first electrically conductive plate; and
an integrally formed structure made from single-crystal silicon semiconductor material and having a diaphragm and a rim that extend entirely around the periphery of the diaphragm and mechanically supports the diaphragm in a nominal position parallel to and at a predetermined nominal distance from the first plate, the diaphragm and rim being electrically conductive and heavily impregnated with at least a first material which alters an etching characteristic thereof in comparison to single-crystal material which is identical to the heavily impregnated material of the diaphragm and rim except for containing substantially less of such first material, the diaphragm constituting a second electrically conductive plate, and being sufficiently thin relative to its overall size to allow it to respond to a mechanical force applied which is thereto in the form of changing pressure in a range designed to be measured by said transducer, thereby changing the capacitance of the parallel place capacitor.

18. A transducer as in claim 17, wherein the rim and diaphragm are formed from a single wafer of single-crystal material and the nominal width of the rim is at least three times smaller than the nominal thickness of the wafer from which it is made.

19. A transducer as in claim 18 wherein the nominal thickness of the rim is no more than about 80 microns, and the nominal height of the rim is no more than about 12 microns.

20. A transducer as in claim 18, wherein the nominal thickness of the single-crystal material of the diaphragm is no more than about two microns.

21. A transducer as in claim 18, wherein the nominal predetermined distance between the first and second parallel plates is less than five microns.

22. A transducer as in claim 18, further comprising:

a support substrate having least one substantially flat surface on a first side thereof, with the first electrically conductive plate formed on the first side of the substrate, and a conductive trace formed on the first side of the substrate adjacent to and electrically isolated from the first conductive plate, and wherein the rim extends at least around a substantial portion of the periphery of the diaphragm and the rim is in electrical contact with the conductive trace.

23. A transducer as in claim 22, wherein the support substrate:

(1) is configured as an elongated rectangular slab,
(2) is no more than about one millimeter long, and
(3) is no more than about one-half millimeter wide.

24. A transducer as in claim 22, wherein the support substrate is a glass material having a coefficient of thermal expansion closely matched to that of single-crystal semiconductor material.

* * * * *

UNITED STATES PATENT AND TRADEMARK OFFICE
CERTIFICATE OF CORRECTION

PATENT NO. : 4,881,410
DATED : Nov. 21, 1989
INVENTOR(S) : Wise et al

It is certified that error appears in the above-identified patent and that said Letters Patent is hereby corrected as shown below:

Column 1, line 46, delete "sensor" and insert ---- sensors ----.

Column 1, line 65, delete "sensor" and insert ---- sensors ----.

Column 2, line 48, after "would" insert ---- be ----.

Column 3, line 39, delete "in" and insert ---- and ----.

Column 3, line 40, delete "comprising" and insert ---- comprises ----.

Column 3, line 68, delete "and" and insert ---- are ----.

Column 4, line 1, delete "alter" and insert ---- alters ----.

Column 4, line 30, after "to" insert ---- be ----.

Column 4, line 31, after "designate" insert ---- identical ----.

Column 4, line 41, after "glass" insert ---- support ----.

Column 5, line 32, after "30" insert a comma ---- , ----.

Column 5, line 41, after "capacitor" insert ---- plate ----.

Column 5, line 43, delete "and" (first occurrence) and insert ---- end ----.

Column 5, line 48, delete "about" and insert ---- abut ----.

UNITED STATES PATENT AND TRADEMARK OFFICE
CERTIFICATE OF CORRECTION

PATENT NO. : 4,881,410

DATED : Nov. 21, 1989

INVENTOR(S) : Wise et al

It is certified that error appears in the above-identified patent and that said Letters Patent is hereby corrected as shown below:

Column 5, line 55, delete "an" and insert ---- and ----.

Column 6, line 17, delete "eing" and insert ---- being ----.

Column 6, line 32, delete "coatoing" and insert ---- coating ----.

Column 7, line 12, delete "become" and insert ---- becomes ----.

Column 10, line 56, delete "to" (first occurrence) and insert ---- of ----.

Column 10, line 61, delete "gate 298 returns" and insert ---- transistor 270 turns off, ----.

Column 10, line 62, delete "to a low logic level".

Col. 13, line 5, after "130," insert --it--.

Column 14, line 13, after "it" insert ---- will ----.

Signed and Sealed this

Thirteenth Day of July, 1993

Attest:

MICHAEL K. KIRK

*Attesting Officer*

*Acting Commissioner of Patents and Trademarks*